United States Patent
Walden et al.

(10) Patent No.: US 9,534,095 B2
(45) Date of Patent: *Jan. 3, 2017

(54) WATER-ABSORBING POLYMER STRUCTURE HAVING IMPROVED PERMEABILITY AND ABSORPTION UNDER PRESSURE

(71) Applicant: EVONIK DEGUSSA GMBH, Essen (DE)

(72) Inventors: Mirko Walden, Herten (DE); Harald Schmidt, Tonisvorst (DE); Rainer Teni, Moers (DE); Armin Reimann, Willich (DE); Franck Furno, Heiligenhaus (DE); Jorg Issberner, Willich-Neersen (DE); Peter Herbe, Duisburg (DE); Ursula Nielinger, Krefeld (DE); Michael Keup, Essen (DE)

(73) Assignee: Evonik Degussa GmbH, Essen (DE)

( * ) Notice: Subject to any disclaimer, the term of this patent is extended or adjusted under 35 U.S.C. 154(b) by 191 days.

This patent is subject to a terminal disclaimer.

(21) Appl. No.: 14/458,761

(22) Filed: Aug. 13, 2014

(65) Prior Publication Data

US 2014/0350191 A1   Nov. 27, 2014

Related U.S. Application Data

(63) Continuation of application No. 12/297,822, filed as application No. PCT/EP2007/003475 on Apr. 20, 2007, now Pat. No. 8,907,017.

(30) Foreign Application Priority Data

Apr. 21, 2006  (DE) .................. 10 2006 019 157
Apr. 21, 2006  (WO) ................. PCT/EP2006/003694
Apr. 21, 2006  (WO) ................. PCT/EP2006/003695
Apr. 21, 2006  (WO) ................. PCT/EP2006/003696
Aug. 12, 2006  (DE) .................. 10 2006 037 983

(51) Int. Cl.

| | |
|---|---|
| C08F 220/06 | (2006.01) |
| C08F 220/10 | (2006.01) |
| C08J 3/24 | (2006.01) |
| A61L 15/60 | (2006.01) |
| C08F 222/10 | (2006.01) |
| C08L 101/14 | (2006.01) |

(52) U.S. Cl.
CPC .............. *C08J 3/245* (2013.01); *A61L 15/60* (2013.01); *C08F 220/06* (2013.01); *C08F 222/1006* (2013.01); *C08L 101/14* (2013.01); *C08J 2333/02* (2013.01)

(58) Field of Classification Search
CPC ... A61L 15/60; C08F 220/06; C08F 222/1006; C08J 3/245; C08J 2333/02
USPC .................... 525/330.2, 55, 329.8
See application file for complete search history.

(56) References Cited

U.S. PATENT DOCUMENTS

| | | |
|---|---|---|
| 4,043,952 A | 8/1977 | Ganslaw et al. |
| 4,076,663 A | 2/1978 | Masuda et al. |
| 4,131,576 A | 12/1978 | Iovine et al. |
| 4,179,367 A | 12/1979 | Barthell et al. |
| 4,286,082 A | 8/1981 | Tsubakimoto et al. |
| 4,340,706 A | 7/1982 | Obayashi et al. |
| 4,587,308 A | 5/1986 | Makita et al. |
| 5,002,986 A | 3/1991 | Fujiura et al. |
| 5,409,771 A | 4/1995 | Dahmen et al. |
| 5,562,646 A | 10/1996 | Goldman et al. |
| 5,599,335 A | 2/1997 | Goldman et al. |

(Continued)

FOREIGN PATENT DOCUMENTS

| | | |
|---|---|---|
| CN | 1342180 A | 3/2002 |
| DE | 2612846 | 10/1976 |

(Continued)

OTHER PUBLICATIONS

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).
Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).
Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

(Continued)

*Primary Examiner* — Ling Choi
*Assistant Examiner* — Chun-Cheng Wang
(74) *Attorney, Agent, or Firm* — Bernard Lau; Linda S. Li; Jason S. Ngui

(57) ABSTRACT

The present invention relates to a process for the preparation of water-absorbing polymer structures, comprising the following process steps:
i) providing an untreated, water-absorbing polymer structure; and
ii) bringing the untreated, water-absorbing polymer structure into contact with a salt comprising a divalent or higher-valent cation of a metal and at least one organic base as anion.

The invention relates also to the water-absorbing polymer structures obtainable by that process, to water-absorbing polymer structures, to a composite comprising a water-absorbing polymer structure and a substrate, to a process for the preparation of a composite, to the composite obtainable by that process, to chemical products, such as foams, molded articles and fibers comprising water-absorbing polymer structures or a composite, to the use of water-absorbing polymer structures or of a composite in chemical products and to the use of a salt in the treatment of the surface of water-absorbing polymer structures.

15 Claims, No Drawings

(56) References Cited

U.S. PATENT DOCUMENTS

| | | |
|---|---|---|
| 5,610,220 A | 3/1997 | Klimmek et al. |
| 5,669,894 A | 9/1997 | Goldman et al. |
| 5,672,633 A | 9/1997 | Brehm et al. |
| 5,712,316 A | 1/1998 | Dahmen et al. |
| 5,837,789 A | 11/1998 | Stockhausen et al. |
| 5,973,042 A | 10/1999 | Yoshinaga et al. |
| 6,403,700 B1 | 6/2002 | Dahmen et al. |
| 6,605,673 B1 | 8/2003 | Mertens et al. |
| 6,620,889 B1 | 9/2003 | Mertens et al. |
| 6,831,142 B2 | 12/2004 | Mertens et al. |
| 7,157,141 B2 | 1/2007 | Inger et al. |
| 7,179,862 B2 | 2/2007 | Mertens et al. |
| 7,282,262 B2 | 10/2007 | Adachi et al. |
| 7,285,599 B2 | 10/2007 | Mertens et al. |
| 7,507,475 B2 | 3/2009 | Inger et al. |
| 7,541,395 B2 | 6/2009 | Reimann et al. |
| 7,625,957 B2 | 12/2009 | Harren et al. |
| 7,728,045 B2 | 6/2010 | Becker et al. |
| 7,816,426 B2 | 10/2010 | Ahmed et al. |
| 7,833,624 B2 | 11/2010 | Harren et al. |
| 7,863,338 B2 | 1/2011 | Becker et al. |
| 7,939,597 B2 | 5/2011 | Bub et al. |
| 8,048,942 B2 | 11/2011 | Fricker et al. |
| 8,063,118 B2 | 11/2011 | Ahmed et al. |
| 8,063,121 B2 | 11/2011 | Fricker et al. |
| 8,071,202 B2 | 12/2011 | Furno et al. |
| 8,198,385 B2 | 6/2012 | Gartner et al. |
| 8,236,876 B2 | 8/2012 | Ahmed et al. |
| 8,252,873 B1 | 8/2012 | Gartner et al. |
| 8,258,249 B2 | 9/2012 | Bub et al. |
| 8,349,913 B2 | 1/2013 | Harren et al. |
| 8,357,766 B2 | 1/2013 | Fricker et al. |
| 8,372,920 B2 | 2/2013 | Walden |
| 8,445,596 B2 | 5/2013 | Mertens et al. |
| 8,653,210 B2 | 2/2014 | Fricker et al. |
| 8,653,320 B2 | 2/2014 | Furno et al. |
| 8,658,146 B2 | 2/2014 | Furno et al. |
| 8,686,216 B2 | 4/2014 | Wattebled et al. |
| 8,703,450 B2 | 4/2014 | Bub et al. |
| 8,907,017 B2 * | 12/2014 | Walden .............. A61L 15/60 525/221 |
| 2003/0207997 A1 * | 11/2003 | Mertens .............. A61L 15/48 525/244 |
| 2006/0029782 A1 | 2/2006 | Harren et al. |
| 2006/0057389 A1 | 3/2006 | Reimann et al. |
| 2007/0066754 A1 | 3/2007 | Loeker et al. |
| 2007/0106239 A1 | 5/2007 | Riegel et al. |
| 2007/0129495 A1 | 6/2007 | Mertens et al. |
| 2008/0032888 A1 | 2/2008 | Nakamura et al. |
| 2008/0221277 A1 | 9/2008 | Walden et al. |
| 2008/0280128 A1 | 11/2008 | Furno et al. |
| 2009/0105389 A1 | 4/2009 | Walden et al. |
| 2010/0036004 A1 | 2/2010 | Harren et al. |
| 2010/0057027 A1 | 3/2010 | Furno et al. |
| 2012/0001122 A1 | 1/2012 | Wattebled et al. |
| 2012/0145956 A1 | 6/2012 | Walden et al. |
| 2012/0302445 A1 | 11/2012 | Rudolph et al. |
| 2014/0045683 A1 | 2/2014 | Loick et al. |
| 2014/0054497 A1 | 2/2014 | Wattebled et al. |
| 2014/0121322 A1 | 5/2014 | Fricker et al. |
| 2014/0180234 A1 | 6/2014 | Bub et al. |

FOREIGN PATENT DOCUMENTS

| | | |
|---|---|---|
| DE | 2706135 | 8/1978 |
| DE | 2840010 A1 | 6/1979 |
| DE | 3503458 | 8/1985 |
| DE | 3713601 A1 | 11/1988 |
| DE | 4020780 | 8/1991 |
| DE | 4244548 | 7/1994 |
| DE | 4418818 | 1/1995 |
| DE | 4333056 | 3/1995 |
| DE | 19529348 A1 | 2/1997 |
| DE | 19646484 A1 | 5/1997 |
| DE | 19909653 A1 | 9/2000 |
| DE | 19909838 A1 | 9/2000 |
| DE | 10249821 A1 | 5/2004 |
| DE | 102004005417 A1 | 8/2004 |
| DE | 10334286 A1 | 3/2005 |
| DE | 102006037983 | 2/2008 |
| EP | 0752892 A1 | 1/1997 |
| EP | 1616581 A1 | 1/2006 |
| JP | 51-136588 A | 11/1976 |
| JP | 61-060631 A | 3/1986 |
| JP | 61-257235 A | 11/1986 |
| JP | 02-227435 A | 9/1990 |
| JP | 09-510889 A | 11/1997 |
| JP | 2002179935 A | 6/2002 |
| JP | 2002-538275 A | 11/2002 |
| JP | 2003-529647 A | 10/2003 |
| JP | 2003277637 A | 10/2003 |
| JP | 2004-261796 A | 9/2004 |
| JP | 2005-344103 A | 12/2005 |
| JP | 2009-534482 A | 9/2009 |
| WO | 9522356 A1 | 8/1995 |
| WO | 9605234 A1 | 2/1996 |
| WO | 9934843 A1 | 7/1999 |
| WO | 0053664 A1 | 9/2000 |
| WO | 2004037903 A2 | 5/2004 |
| WO | 2006111402 A2 | 10/2006 |

OTHER PUBLICATIONS

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

Furno et al., U.S. Appl. No. 14/448,188, filed Jul. 31, 2014.

German language International Search Report mailed on Jul. 23, 2007 in PCT/EP2007/003475 (9 pages).

German language Written Opinion mailed on Jul. 23, 2007 in PCT/EP2007/003475 (18 pages).

Henn et al., U.S. Appl. No. 14/352,171, filed Apr. 16, 2014.

Vorholt et al., U.S. Appl. No. 14/364,313, filed Jun. 11, 2014.

Vorholt et al., U.S. Appl. No. 14/364,346, filed Jun. 11, 2014.

Walden et al., Japanese Patent Application No. 2009-505786 (Pub. No. 2009-534482), Notification from Japanese Patent Office concerning offering of information from third party (17 pages).

Wattebled et al., U.S. Appl. No. 14/352,091, filed Apr. 16, 2014.

* cited by examiner

WATER-ABSORBING POLYMER STRUCTURE HAVING IMPROVED PERMEABILITY AND ABSORPTION UNDER PRESSURE

This application is a divisional application of U.S. application Ser. No. 12/297,822 filed 6 Jan. 2009, currently pending, which is a national stage application under 35 U.S.C. 371 of International Application No. PCT/EP2007/003475 filed 20 Apr. 2007, and claims priority to German Application No. DE 10 2006 019 157.9 filed 21 Apr. 2006; International Application No. PCT/EP2006/003695 filed 21 Apr. 2006; International Application No. PCT/EP2006/003694 filed 21 Apr. 2006; International Application No. PCT/EP2006/003696 filed 21 Apr. 2006; and German Application No. DE 10 2006 037 983.7 filed 12 Aug. 2006, the disclosures of which are expressly incorporated herein by reference.

BACKGROUND

The present invention relates to a process for the preparation of water-absorbing polymer structures, to the water-absorbing polymer structures obtainable by that process, to water-absorbing polymer structures, to a composite comprising a water-absorbing polymer structure and a substrate, to a process for the preparation of a composite, to the composite obtainable by that process, to chemical products, such as foams, molded articles, and fibers comprising water-absorbing polymer structures or a composite, to the use of water-absorbing polymer structures or of a composite in chemical products, and to the use of a salt in the treatment of the surface of water-absorbing polymer structures.

Superabsorbers are water-insoluble, crosslinked polymers which are able to absorb large amounts of aqueous fluids, especially body fluids, such as urine or blood, with swelling and the formation of hydrogels, and to retain such fluids under a certain pressure. By virtue of those characteristic properties, such polymers may be used for incorporation into sanitary articles, such as, for example, baby's diapers, incontinence products, or sanitary towels.

The preparation of superabsorbers is generally carried out by free-radical polymerization of acid-group-carrying monomers in the presence of crosslinkers. It is possible for polymers, having different absorber properties, to be prepared by the choice of the monomer composition, the crosslinkers, and the polymerization conditions, and of the processing conditions for the hydrogel obtained after the polymerization. Further possibilities are offered by the preparation of graft polymerizates, for example using chemically modified starch, cellulose, and polyvinyl alcohol according to DE-OS 26 12 846.

Commercially available superabsorbers are essentially crosslinked polyacrylic acids, or crosslinked starch/acrylic acid graft polymerizates in which the carboxyl groups have been partially neutralized with sodium hydroxide solution or potassium hydroxide solution.

For aesthetic reasons and environmental considerations, there is an increasing tendency to make sanitary articles smaller and thinner. In order to maintain the total retention capacity of the sanitary articles, the requirements of smaller and thinner can be met only by reducing the proportion of high-volume fluff. As a result, the superabsorber has to fulfill further functions in respect of transport and distribution of fluid, which can be summarized as permeability properties.

Permeability, in the case of superabsorber materials, generally means the ability in the swollen state to transport added fluids and distribute them three-dimensionally. In the swollen superabsorber gel, that process takes place by means of capillary transport through interstices between the gel particles. Transport of fluid by swollen superabsorber particles themselves obeys the laws of diffusion and is a very slow process which, in the situation of being used in a sanitary article, plays no role in the distribution of the fluid. In the case of superabsorber materials unable to affect capillary transport on account of lack of gel stability, separation of the particles from one another was ensured by embedding those materials in a fiber matrix, the gel blocking phenomenon being avoided. In new generation nappy/diaper structures, only very little fiber material, or none at all, is present in the absorber layer to assist the transport of fluid. The superabsorbers used therein must accordingly have sufficiently high stability in the swollen state so that the swollen gel still has a sufficient amount of capillary spaces through which fluid can be transported.

In order to obtain superabsorber materials having high gel stability, one possibility is to increase the degree of crosslinking of the polymer, which inevitably results in a reduction in swelling ability and retention capacity. An optimized combination of different crosslinkers and co-monomers, as described in DE 196 46 484, is able to improve the permeability properties but not to a level which allows, for example, a layer possibly consisting only of superabsorbers to be incorporated into a nappy/diaper structure.

Furthermore, methods for the after treatment of the surface of polymer particles can be used to improve the superabsorber properties. Surface treatments known from the prior art include, for example, post-crosslinking of the absorbent polymer structure at the surface, bringing the surface into contact with inorganic compounds, and post-crosslinking of the surface in the presence of inorganic compounds.

For example, DE 199 09 653 A1 and DE 199 09 838 A1 disclose powdered polymerizates post-crosslinked at the surface which absorb water, aqueous, or serous fluids, or blood, which polymerizates are based on acid-group-carrying monomers and have been coated with a surface post-crosslinking agent and, for example, aluminum sulphate in aqueous solution and post-crosslinked. The polymerizates disclosed in that prior art have advantageous absorption properties in comparison with conventional polymerizates, especially a high degree of permeability.

DE 102 49 821 A1 describes likewise powdered, water-absorbing polymer structures that are post-crosslinked at the surface having a high degree of permeability, which polymer structures have been obtained by surface treatment of untreated, water-absorbing polymer structures with a mixture of a crosslinker and an inorganic sol, for example silicic acid sol.

The disadvantage of the surface modification measures known from the prior art, especially the treatment of water-absorbing polymer structures with inorganic salts or inorganic sols for the purposes of improving permeability, lies, however, particularly in the fact that the increase in permeability that is observed is frequently also associated with a significant reduction in absorption capacity under pressure. That reduction in absorption capacity under pressure often results in the hygiene articles' having an increased tendency to leak after being wetted once or, especially, several times by the user.

The problem underlying the present invention was to overcome the disadvantages arising from the prior art.

The problem underlying the present invention was especially to provide a superabsorber which firstly promotes the transport of aqueous fluids, such as urine, in hygiene articles such as absorbent layers or cores, particularly for diapers, having high superabsorber concentrations, and thus to increase the wearing comfort of such hygiene articles.

A further problem underlying the present invention was to provide a process by which such advantageous superabsorbers and a composite comprising such superabsorbers can be produced.

Another problem underlying the present invention was to provide hygiene articles that are as thin as possible and have a high content of water-absorbing polymer structures and that are characterized by good in-use properties.

SUMMARY

A solution to the above-mentioned problems is provided by a process for the preparation of a water-absorbing polymer structure, comprising the following process steps:
i) providing an untreated, water-absorbing polymer structure;
ii) bringing the untreated, water-absorbing polymer structure into contact with a salt comprising a divalent or higher-valent cation of a metal and at least one organic base as anion, the water-absorbing polymer structures being brought into contact with the salt optionally at a temperature in a range of from about 30 to about 210° C., or from about 100 to about 200° C., or from about 160 to about 190° C.

In accordance with another embodiment of the process of the invention, at least one, or at least two, or all three of the following conditions (a1) to (a3) are fulfilled:
(a1) the untreated, water-absorbing polymer structure is not brought into contact with an oxide of a metal, or not brought into contact with an oxide of a transition metal, or not brought into contact with an oxide of zinc;
(a2) the untreated, water-absorbing polymer structure is not brought into contact with a polycation, or not brought into contact with an organic polycation that has a molecular weight of more than about 3000 g/mol, or not brought into contact with a polymer of diallyldimethylammonium chloride;
(a3) the untreated, water-absorbing polymer structure has a retention of less than about 37.5 g/g determined in accordance with the test method described herein.

Entirely surprisingly, it has been found that the fall in absorption under a pressure load that is frequently observed when water-absorbing polymer structures are surface-modified with permeability-enhancing agents may be reduced by the use of salts as permeability-enhancing agents comprising a divalent or higher-valent cation of a metal and at least one organic base as anion.

"Untreated" in the context of the present invention means that the water-absorbing polymer structures provided in process step i) have not yet been brought into contact with the salt comprising a divalent or higher-valent cation of a metal and at least one organic base as anion. The term "untreated" does not, however, exclude the water-absorbing polymer structures' having been modified by means of other surface modification measures, such as, for example, surface post-crosslinking.

As untreated, water-absorbing polymer structures provided in process step i) there are fibers, foams, or particles.

DETAILED DESCRIPTION

Polymer fibers according to the invention may be so dimensioned that they can be incorporated into or as yarns for textiles and also directly into textiles. The polymer fibers may have a length in the range of from about 1 to about 500 mm, or from about 2 to about 500 mm, or from about 5 to about 100 mm and a diameter from about 1 to about 200 denier, or from about 3 to about 100 denier, from about 5 to about 60 denier.

Polymer particles according to the invention may be so dimensioned that they have an average particle size in accordance with ERT 420.2-02 in the range of from about 10 to about 3000 nm, or from about 20 to about 2000 nm, or from about 150 to about 850 nm or from about 150 to about 600 nm. The proportion of polymer particles may have a particle size of from about 300 to about 600 nm to be at least about 30% by weight, or at least about 40% by weight, or at least about 50% by weight, based on the total weight of the post-crosslinked, water-absorbing polymer particles.

In another embodiment of the water-absorbing polymer structures provided in process step i), the polymer structures may be based on
($\alpha$1) from about 20 to about 99.999% by weight, or from 55 to about 98.99% by weight, or from 70 to about 98.79% by weight, polymerized, ethylenically unsaturated, acid-group-carrying monomers or their salts or polymerized, ethylenically unsaturated monomers containing a protonated or quaternized nitrogen atom, or mixtures thereof, including mixtures containing at least ethylenically unsaturated, acid-group-containing monomers, such as acrylic acid;
($\alpha$2) from 0 to about 80% by weight, or from 0 to about 44.99% by weight, or from 0.1 to about 44.89% by weight, polymerized, monoethylenically unsaturated monomers copolymerizable with ($\alpha$1);
($\alpha$3) from 0.001 to about 5% by weight, or from 0.01 to about 3% by weight, or from 0.01 to about 2.5% by weight, of one or more crosslinkers;
($\alpha$4) from 0 to about 30% by weight, or from 0 to about 5% by weight, or from 0.1 to about 5% by weight, of a water-soluble polymer;
($\alpha$5) from 0 to about 20% by weight, or from 2.5 to about 15% by weight, or from about 5 to about 10% by weight, water, and
($\alpha$6) from 0 to about 20% by weight, or from 0 to about 10% by weight, or from 0.1 to about 8% by weight, of one or more auxiliaries, the sum of the amounts by weight ($\alpha$1) to ($\alpha$6) being 100% by weight.

The monoethylenically unsaturated, acid-group-containing monomers ($\alpha$1) may be partially or fully neutralized, or partially neutralized. At least about 25 mol %, or at least 50 mol %, or especially from about 50 to about 80 mol %, of the monoethylenically unsaturated, acid-group-containing monomers are neutralized. In this connection reference is made to DE 195 29 348 A1. The neutralization may also be effected partially or completely after the polymerization. Furthermore, the neutralization may be effected with alkali metal hydroxides, alkaline earth metal hydroxides, ammonia, and also carbonates and bicarbonates. Also possible is any further base that forms a water-soluble salt with the acid. Mixed neutralization with different bases is also a possibility, such as with ammonia and alkali metal hydroxides, such as with sodium hydroxide and with ammonia.

Furthermore, in a polymer the free acid groups may predominate, so that the polymer may have a pH in the acidic range. Such an acidic water-absorbing polymer may be neutralized, at least partially, by a polymer having free basic groups, such as amine groups that are basic in comparison with the acidic polymer. Those polymers are known in the literature as "Mixed-Bed Ion-Exchange Absorbent Polymers" (MBIEA polymers) and are disclosed inter alia in WO 99/34843 A1. MBIEA polymers may generally be a composition containing on the one hand basic polymers that are capable of exchanging anions and on the other hand a polymer that is acidic in comparison with the basic polymer, which acidic polymer is capable of exchanging cations. The basic polymer has basic groups and is typically obtained by polymerization of monomers carrying basic groups or groups that can be converted into basic groups. Such monomers may include those having primary, secondary, or tertiary amines or the corresponding phosphines or at least two of the above functional groups. That group of monomers may include ethyleneamine, allylamine, diallylamine, 4-aminobutene, alkyloxycycline, vinyl-formamide, 5-aminopentene, carbodiimide, formaldacine, melamine, and the like, as well as the secondary or tertiary amine derivatives thereof.

Ethylenically unsaturated, acid-group-containing monomers ($\alpha$1) may include those compounds mentioned as ethylenically unsaturated, acid-group-containing monomers ($\alpha$1) in WO 2004/037903 A2, wherein such ethylenically unsaturated, acid-group-containing monomers ($\alpha$1) are herewith incorporated as reference and part of the disclosure. Ethylenically unsaturated, acid-group-containing monomers ($\alpha$1) include acrylic acid and methacrylic acid.

In accordance with an embodiment of the process of the invention there are used untreated, water-absorbing polymer structures in which the monoethylenically unsaturated monomers ($\alpha$2) copolymerizable with ($\alpha$1) are acrylamides, methacrylamides or vinylamides.

(Meth)acrylamides, in addition to acrylamide and methacrylamide, may include alkyl-substituted (meth)acrylamides or aminoalkyl-substituted derivatives of meth(acrylamide), such as N-methylol(meth)acrylamide, N,N-dimethylamino-(meth)acrylamide, dimethyl(meth)acrylamide or diethyl(meth)acrylamide. Possible vinylamides are, for example, N-vinylamides, N-vinylformamides, N-vinylacetamides, N-vinyl-N-methylacetamides, N-vinyl-N-methylformamides, vinylpyrrolidone.

In accordance with another embodiment of the process of the invention there are used water-absorbing polymer structures in which the monoethylenically unsaturated monomers ($\alpha$2) copolymerizable with ($\alpha$1) are water-soluble monomers, such as alkoxypolyalkylene oxide (meth)acrylates and methoxypolyethylene glycol (meth)acrylates.

Furthermore, as monoethylenically unsaturated monomers ($\alpha$2) copolymerizable with ($\alpha$1) include monomers dispersible in water. Monomers dispersible in water may include acrylic acid esters and methacrylic acid esters, such as methyl (meth)acrylate, ethyl (meth)acrylate, propyl (meth)acrylate or butyl (meth)acrylate.

The monoethylenically unsaturated monomers ($\alpha$2) copolymerizable with ($\alpha$1) also include methyl polyethylene glycol allyl ether, vinyl acetate, styrene, and isobutylene.

Crosslinkers ($\alpha$3) may include those compounds mentioned as crosslinkers ($\alpha$3) in WO 2004/037903 A2 including water-soluble crosslinkers, such as N,N'-methylene bisacrylamide, polyethylene glycol di(meth)acrylates, triallylmethylammonium chloride, tetraallylammonium chloride, as well as allyl nonaethylene glycol acrylate prepared with 9 mol of ethylene oxide per mol of acrylic acid.

As water-soluble polymers ($\alpha$4) the polymer structures may comprise, such as incorporated by polymerization, water-soluble polymers, such as partially or fully hydrolyzed polyvinyl alcohol, polyvinylpyrrolidone, starch, or starch derivatives, polyglycols, or polyacrylic acid. The molecular weight of those polymers is not critical provided they are water-soluble. Water-soluble polymers are starch or starch derivatives or polyvinyl alcohol. The water-soluble polymers include synthetic polymers, such as polyvinyl alcohol, may also be used as grafting base for the monomers to be polymerized.

As auxiliaries ($\alpha$6) the polymer structures may comprise diluents, odor-binders, surface-active agents, or antioxidants as well as the additives used for preparing the polymer structures (initiators etc.).

In another embodiment of the water-absorbing polymer structures provided in process step i), at least about 50% by weight, or at least about 70% by weight, or at least about 90% by weight, of the polymer structures are based on carboxylate-group-carrying monomers. Component ($\alpha$1) may consist of at least about 50% by weight, or at least about 70% by weight, acrylic acid, of which at least about 20 mol %, or at least about 50 mol %, or from about 60 to about 85 mol %, have been neutralized.

The untreated, water-absorbing polymer structures may be produced from the above-mentioned monomers, comonomers, crosslinkers, water-soluble polymers, and auxiliaries by different methods of polymerization. For example, there may mass polymerization, which may be carried out in kneader reactors, such as extruders, solution polymerization, spray polymerization, inverse emulsion polymerization, and inverse suspension polymerization.

Solution polymerization may be carried out in water as solvent. Solution polymerization can be carried out continuously or discontinuously. A broad spectrum of possible variants in respect of reaction conditions, such as temperatures and the nature and amount of the initiators and of the reaction solution, can be found in the prior art. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33056, DE 44 18 818.

The polymerization is initiated by an initiator. For initiators it is possible to use any initiators forming free radicals under the polymerization conditions that are customarily used for the preparation of superabsorbers. It is also possible to initiate polymerization by the action of electron beams on the polymerizable, aqueous mixture. The polymerization may also be triggered in the absence of initiators of the above-mentioned kind, however, by the action of high-energy radiation in the presence of photoinitiators. Polymerization initiators may be present in dissolved form or dispersed form in a solution of monomers according to the invention. Initiators that come into consideration may include all compounds that decompose into free radicals known to the person skilled in the art, including, in particular, the initiators already mentioned as possible initiators in WO 2004/037903 A2.

Preparation of the water-absorbing polymer structures may use a redox system consisting of hydrogen peroxide, sodium peroxodisulphate, and ascorbic acid.

Inverse suspension and emulsion polymerization may also be used for the preparation of the polymer structures. In accordance with those processes, an aqueous, partially neutralized solution of monomers ($\alpha$1), and ($\alpha$2), containing water-soluble polymers and auxiliaries, may be dispersed in a hydrophobic, organic solvent with the aid of protective colloids, and/or emulsifiers, and the polymerization may be started by free radical initiators. The crosslinkers may either dissolved in the monomer solution and metered in together with the monomer solution or are added separately, and optionally during the polymerization. If desired, the addition of a water-soluble polymer ($\alpha$4) as grafting base may be effected by way of the monomer solution or by direct addition into the oil phase. The water is then removed from the mixture azeotropically and the polymerizate is filtered off.

Furthermore, both in the case of solution polymerization and in the case of inverse suspension and emulsion polymerization, the crosslinking may be effected by incorporating by polymerization the polyfunctional crosslinker dissolved in the monomer solution and/or by reacting suitable crosslinkers with functional groups of the polymer during the polymerization steps. The processes are described, for example, in the publications U.S. Pat. No. 4,340,706, DE 37 13 601, DE 28 40 010 and WO 96/05234 A1.

The hydrogels obtained after polymerization in the case of solution polymerization or the inverse suspension and emulsion polymerization may be dried in a further process step.

In the case of solution polymerization, the hydrogels may be comminuted before drying. Such comminution may be effected by comminuting devices known to the person skilled in the art, such as, for example, a mincer.

The drying of the hydrogel may be effected in suitable dryers or ovens. Rotary tube furnaces, fluidized bed dryers, plate dryers, paddle dryers, and infrared dryers may be mentioned by way of example. Furthermore, the hydrogel may be dried to a water content of from about 0.5 to about 25% by weight, or from about 1 to about 10% by weight, the drying temperatures usually being in a range of from about 100 to about 200° C.

The water-absorbing polymer structures obtained after drying, obtained by solution polymerization, may then be ground in a further process step and screened to the desired particle size mentioned at the beginning. The grinding of the dried, water-absorbing polymer structures may be effected in suitable mechanical comminuting devices, such as, for example, a ball mill.

In another embodiment, the untreated absorbent polymer structure provided in process step i) of the process may exhibit at least one of the following properties (ERT=EDANA Recommended Test):

(A) the maximum absorption according to ERT 440.2-02 (in the case of particles, determined for the entire particle size fraction) of 0.9% by weight NaCl solution lies in a range of at least from about 10 to about 1000 g/g, or from about 20 to about 500 g/g, or from about 50 to about 100 g/g;

(B) the extractable portion according to ERT 470.2-02 (in the case of particles, determined for the entire particle size fraction) after 16 hours is less than about 30% by weight, or less than about 20% by weight, or less than about 15% by weight, in each case based on the untreated, water-absorbing polymer structure;

(C) the bulk density according to ERT 460.2-02 (in the case of particles, determined for the entire particle size fraction) may be from about 300 to about 1000 g/l, or from about 400 to about 900 g/l, or from about 500 to about 800 g/l;

(D) the pH value according to ERT 400.2-02 (in the case of particles, determined for the entire particle size fraction) of 1 g of the water-absorbing polymer primary product in 1 liter of water lies in the range of from about 4 to about 10, or from about 4.5 to about 9, or from about 5 to about 8;

(E) the absorption determined according to ERT 442.2-02 (in the case of particles, for the entire particle fraction) against a pressure of 0.3 psi lies in a range of from about 10 to about 26 g/g, or from about 13 to about 25 g/g, or from about 13.5 to about 24 g/g;

(F) the retention determined according to ERT 441.2-02 (in the case of particles, for the entire particle fraction), referred to as CRC, lies from about 20 to about 50 g/g, or from about 25 to about 45 g/g, or from about 27 to about 40 g/g.

In accordance with another embodiment of the process of the invention, in process step i) the polymer structures provided may be characterized by the following properties or combinations of properties: (A), (B), (C), (D), (E), (F), (A)(E), (B)(E), (C)(E), (D)(E), (E)(F), (B)(E), (B)(F), (E)(F)(G).

In process step ii) of the process according to the invention, the untreated, water-absorbing polymer structures provided in process step i) may be brought into contact with a salt comprising a divalent or higher-valent cation of a metal, and at least one organic base as anion.

The divalent or higher-valent cation of a metal may be selected from the group consisting of $Mg^{2+}$, $Ca^{2+}$, $Ba^{2+}$, $Al^{3+}$, $Fe^{2+}$, $Fe^{3+}$, $Ga^{3+}$, $Ti^{4+}$, $Zr^{4+}$, $Cu^{2+}$, and $Zn^{2+}$.

The organic base may be an at least partially deprotonated mono-, di- or tri-carboxylic acid, special preference being given to deprotonated monocarboxylic acids. Also included may be hydroxycarboxylic acids, such as at least partially deprotonated mono-, di- or hydroxy-tri-carboxylic acids, and monohydroxycarboxylic acids.

Anions may include the corresponding bases of the following acids: anisic acid, benzoic acid, formic acid, valeric acid, citric acid, glyoxylic acid, glycolic acid, glycerolphosphoric acid, glutaric acid, chloracetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidinoacetic acid, malic acid, isothionic acid, methylmaleic acid, adipic acid, itaconic acid, crotonic acid, oxalic acid, salicylic acid, gluconic acid, gallic acid, sorbic acid, gluconic acid, fatty acids, such as stearic acid and adipic acid, and p-hydroxybenzoic acid, including tartrate and lactate.

In another embodiment of the process of the invention, in process step ii) the salt used is a salt that comprises aluminum lactate. At least about 50% by weight, or at least about 75% by weight, or 100% by weight, of that salt are based on aluminum lactate. In addition to the aluminum lactate, it may be for one or two or more further cations to be present. Such a cation may be selected from monovalent, divalent or higher-valent cations of a metal selected in turn from the group consisting of $Mg^{2+}$, $Ca^{2+}$, $Ba^{2+}$, $Al^{3+}$, $Fe^{2+}$, $Fe^{3+}$, $Ga^{3+}$, $Ti^{4+}$, $Zr^{4+}$, $Cu^{2+}$, and $Zn^{2+}$. Moreover, in addition to the aluminum lactate, it is also possible for further anions to be present in the salt. Furthermore, in addition to aluminum lactate, it is also possible for oxides or mixed oxides of further metals to be present, such as being given to the oxides of the metal ions mentioned in this section. For example, in connection with the solution containing the salt, the solution may contain a secondary salt an alkali metal or alkaline earth metal salt, or an alkali metal salt of one of the above-mentioned anions, or the anion of the main salt chiefly present in the solution. These include lithium lactate and sodium lactate. The amount of the secondary salt may be from 0.001 to about 25% by weight, or from 0.01 to about 17% by weight, or from about 0.1 to about 12% by weight, in each case based on the main salt.

In another embodiment of the process according to the invention, an anion different from the organic base may be used. The anion may be an inorganic base. That inorganic base may be a deprotonated inorganic acid. Such acids are able to release two or more protons. They include acids containing sulphur, nitrogen, or phosphorus, such as acids containing sulphur or phosphorus. Acids containing sulphur, especially sulphuric acid and accordingly sulphate as the salt thereof, may be used for the base. In accordance with another embodiment of the process of the invention, in process step ii) there may be used as further salt a salt comprising aluminum sulphate. At least about 50% by weight, or at least about 75% by weight, or 100% by weight, of that salt may be based on aluminum sulphate. The two different anions may be used in a ratio of from about 1:100 to about 100:1, or in a ratio of from about 1:10 to about 10:1, or from about 1:5 to about 5:1.

Furthermore, in another embodiment according to the invention for the untreated, water-absorbing polymer structure in process step ii) to be brought into contact with from 0.001 to about 10% by weight, or from 0.01 to about 7.5% by weight, or from 0.1 to about 5% by weight, of the salt or salts, in each case based on the weight of the untreated, water-absorbing polymer structure.

The salt may be brought into contact with the untreated, water-absorbing polymer structure in process step ii) of the process according to the invention by mixing together the two components, suitable mixing apparatus for the purpose being such as a Patterson Kelley mixer, DRAIS turbulent mixer, Lodige mixer, Ruberg mixer, screw mixer, plate mixer, and fluidized bed mixer or continuously operating vertical mixers in which the polymer structure is mixed at high frequency by means of rotating blades (Schugi mixer).

Furthermore, the salt may be brought into contact with the untreated, water-absorbing polymer structure in the form of a fluid $F_1$, comprising a solvent and the salt dissolved or dispersed in that solvent, or in dry form as a salt powder. Suitable solvents, in addition to water, may be water-miscible, organic solvents such as, for example, methanol, ethanol, 1-propanol, 2-propanol, 1,2-propanediol, 1,3-propanediol, 1-butanol, 2-butanol, tert-butanol, isobutanol, or mixtures of organic solvents or mixtures of water with one or more of those organic solvents, such as being given to water as solvent. If the untreated, water-absorbing polymer structure is brought into contact with the fluid $F_1$ comprising the solvent and the salt, such that the fluid $F_1$ may contain the salt in an amount in a range of from about 0.1 to about 50% by weight, or from about 1 to about 40% by weight, or from about 5 to about 25% by weight, in each case based on the total weight of the fluid $F_1$.

In accordance with another embodiment of the process of the invention, the untreated, water-absorbing polymer structure may be brought into contact with the salt in process step ii) in the presence of at least about 0.01% by weight, and at most about 15% by weight, or at least about 0.1 and at most about 10% by weight, or at least about 0.5 and at most about 5% by weight, or at least about 1 and at most about 2.5% by weight, of a solvent, the above-mentioned percentages by weight being based on the weight of the untreated, water-absorbing polymer structure.

It can also be advantageous for the untreated, water-absorbing polymer structure to be brought into contact with the salt in process step ii) at a temperature in a range of from about 30 to about 210° C., or from about 50 to about 200° C., or from about 160 to about 195° C. Contact may be made over a period from about 10 to about 300 minutes, or from about 15 to about 180 minutes, or from about 20 to about 120 minutes.

In accordance with another embodiment of the process of the invention for the treatment of the surface of water-absorbing polymer structures, in process step ii) the untreated, water-absorbing polymer structures may be brought into contact with the salt, the salt being present in powder form. In that case, the water-absorbing polymer structure may be brought into contact with the salt in the absence of a solvent.

In another embodiment of the process according to the invention for the preparation of water-absorbing polymer structures, the process may comprise the following process steps:
i) providing the water-absorbing polymer structure that is untreated but is may be already post-crosslinked at the surface;
ii) bringing the water-absorbing polymer structure that is untreated but already post-crosslinked at the surface into contact with a finely particulate component comprising the salt at a temperature from about 30 to about 300° C., or from about 100 to about 250° C., or from about 110 to about 200° C., or from about 115 to about 180° C. In a different form, contact may be made at a temperature of from about 30 to about 200° C., or from about 50 to about 160° C., or from about 50 to about 160° C., or from about 100 to about 140° C.

In this embodiment, at least about 50% by weight, or at least about 75% by weight, or at least about 95% by weight, or at least about 99% by weight, of the powdered salt may have an average particle diameter (weight average) from about 10 to about 1000 µm, or from about 50 µm to about 800 µm, or from about 100 to about 600 µm, or from about 200 to about 400 µm, in each case determined by methods of particle size determination known to the person skilled in the art, for example by sieve analysis or by means of a Coulter Counter.

Furthermore, the finely particulate component may also contain a binder in addition to the powdered salt, such that the binder may be in particulate form and, at least about 50% by weight, or at least about 75% by weight, or at least about 95% by weight, or at least about 99% by weight, of the binder being based on particles having an average particle diameter (weight average) of from about 10 to about 1000 µm, or from about 50 µm to about 800 µm, or from about 100 to about 600 µm, or from about 200 to about 400 µm, in each case determined by methods of particle size determination known to the person skilled in the art, for example by sieve analysis or by means of a Coulter Counter.

In accordance with another embodiment of the invention, the salt may be added as a solid to the post-crosslinking solution, wherein the salt may be present in dissolved form in the post-crosslinking solution at the latest on addition of the post-crosslinking solution to the untreated, but not yet post-crosslinked, polymer structure. The resulting mixture containing untreated polymer structure, post-crosslinker, and salt is then subjected to the temperature treatment customary for the post-crosslinking and described herein.

In another embodiment according to the invention, the salt may be added to the post-crosslinking solution in the form of an aqueous solution. As a result, post-crosslinker/salt solutions may be formed which may have a salt concentration in the range of from 1 to about 50% by weight, or from about 10 to about 40% by weight, or from about 15 to about 35% by weight, in each case based on the amount of solvent in the post-crosslinking solution. The resulting mixture containing untreated polymer structure, post-crosslinker and salt may then be subjected to the temperature treatment customary for the post-crosslinking and described herein. The mixture can be stabilized by addition of the secondary salt described in greater detail below including the amounts of secondary salt.

In that connection, the binder may contain an organic compound as a binder main component, wherein the organic compound may be a solid at about 20° C.

The organic compound may be a linear polymer, such as a linear polymer selected from the group comprising polyurethanes, polyesters, polyamides, polyester amides, polyolefins, polyvinyl esters, polyethers, polystyrenes, polyimides, polyether imides, polyimines, sulphur polymers, such as polysulphone, polyacetals, polyoxymethylene, fluorinated plastics such as polyvinylidene fluoride, styrene/olefin copolymers, polyacrylates, ethylene/vinyl acetate copolymers, and mixtures of two or more of the mentioned polymers.

Suitable linear polyethers may include polyalkylene glycols such as polyethylene glycols, polypropylene glycols, poly(ethylene/propylene) glycols having a statistical or block-like arrangement of the ethylene or propylene monomers or mixtures of at least two of those polyalkylene glycols.

Other linear polymers include those polymers mentioned as "thermoplastic adhesives" in DE-A-103 34 286. The disclosure content of DE-A-103 34 286 in respect of and limited to thermoplastic adhesives is herewith incorporated as reference and forms part of the disclosure of the present invention.

If a binder is used in addition to the salt, the untreated, water-absorbing polymer structure may be brought into contact with the finely particulate component at a temperature of from about 30 to about 200° C., or from about 50 to about 160° C., or from about 70 to about 140° C. Those temperatures result also in immobilization of the fine particles on the surface of the untreated, water-absorbing polymer structure.

The amount of binder, if used, may be from 0.0001 to about 5% by weight, or from 0.001 to about 2% by weight, in each case based on the weight of the water-absorbing polymer structure. The ratio by weight between finely particulate component and binder may be of finely particulate component:binder of from about 20:1 to about 1:20, or from about 10:1 to about 1:10, or from about 10:1 to about 2:1.

In the above-described embodiment of the process in which a powdered salt is brought into contact with the water-absorbing polymer structures, the process comprises, in addition of the provision of the untreated, water-absorbing polymer structure in process step i), also the provision of a finely particulate component comprising the powdered salt and, where applicable, the powdered binder. Various process procedures are possible in respect of the way in which the finely particulate component is brought into contact with the untreated, water-absorbing polymer structure.

Furthermore, in connection with the above-described, embodiment in which a powdered salt is brought into contact with the water-absorbing polymer structure, it may be advantageous for process step ii) to be followed by a further process step ii') in which the mixture of untreated, water-absorbing polymer structure and finely particulate component is mixed for a period of from about 10 minutes to about 5 hours, or from about 30 minutes to about 3 hours, in order to facilitate as homogeneous as possible a distribution of the fine particles or the fine particle agglomerates and the absorbent polymer structures, for which purpose mixing devices known to the person skilled in the art may be used. In that further process step, the mixture of untreated, water-absorbing polymer structure and finely particulate component may be introduced into the mixer at the temperature that it has after the immobilization in process step ii), it then being possible to cool the mixture, such as continuously, to a lower temperature, such as to room temperature, in the course of the mixing operation.

In accordance with another embodiment of the process of the invention, the process may comprise the following process step in addition to process steps i) and ii):
iii) post-crosslinking of the water-absorbing polymer structure at the surface,
it being possible to carry out process step iii) before, during or after process step ii).

In the surface post-crosslinking, the dried polymer structures or the not yet dried, but already comminuted hydrogel may be brought into contact with an organic, chemical surface post-crosslinker. The post-crosslinker, such as one that is not liquid under the post-crosslinking conditions, may be brought into contact with the polymer particles or the hydrogel in the form of a fluid $F_2$ comprising the post-crosslinker and a solvent, such as solvents already mentioned as solvent in connection with the fluid $F_1$. Furthermore, the post-crosslinker may be present in the fluid $F_2$ in an amount of from about 5 to about 75% by weight, or from about 10 to about 50% by weight, or from about 15 to about 40% by weight, based on the total weight of the fluid $F_2$.

The polymer structure or the comminuted hydrogel is brought into contact with the fluid $F_2$ comprising the post-crosslinker in the process according to the invention by thorough mixing of the fluid $F_2$ with the polymer structure, suitable mixing apparatus for applying the fluid $F_2$ again being a Patterson Kelley mixer, DRAIS turbulent mixer, Lodige mixer, Ruberg mixer, screw mixer, plate mixer or fluidized bed mixer as well as continuously operating vertical mixers in which the polymer structure is mixed at high frequency by means of rotating blades (Schugi mixer).

In the post-crosslinking, the water-absorbing polymer structure may be brought into contact with at most about 20% by weight, or at most about 15% by weight, or at most about 10% by weight, or at most about 5% by weight, of solvent, such as water, in each case based on the weight of the water-absorbing polymer structure.

In the case of polymer structures in the form of spherical particles, the contact may be made by bringing solely the outer region, but not the inner region, of the particulate polymer structures into contact with the fluid $F_2$ and accordingly with the post-crosslinker.

Post-crosslinkers that may be used in the process according to the invention may be understood as being compounds having at least two functional groups that are able to react with functional groups of a polymer structure in a condensation reaction (=condensation crosslinker), in an addition reaction or in a ring-opening reaction. As post-crosslinkers in the process according to the invention preference is given to those mentioned as crosslinkers of crosslinker classes II in WO 2004/037903 A2.

Such post-crosslinking compounds include condensation crosslinkers such as, diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

After the polymer structures or the hydrogels have been brought into contact with the post-crosslinker or with the fluid $F_2$ comprising the post-crosslinker, may be heated to a temperature of from about 50 to about 300° C., or from about 75 to about 275° C., or from about 150 to about 250° C., so that, with the result that, the outer region of the polymer structures is more highly crosslinked in comparison with the inner region (=post-crosslinking). The duration of the heat treatment may be limited by the risk of destroying the desired property profile of the polymer structures as a result of the action of heat.

The surface modification by means of post-crosslinking described above may be carried out before, during or after process step ii).

If the post-crosslinking is carried out before process step ii), then in process step ii) water-absorbing polymer structures that have already been post-crosslinked at the surface may be brought into contact with the salt either in dry form or in the form of the fluid $F_1$.

If the post-crosslinking is effected during process step ii), first of all the untreated, water-absorbing polymer structures may be brought into contact with the post-crosslinker and the salt
  in each case in the absence of a solvent,
  in the form of fluids $F_1$ and $F_2$,
  in the form of a common fluid $F_3$, comprising the solvent and the post-crosslinker and the salt or
  the salt in the absence of a solvent and the post-crosslinker in the form of the fluid $F_2$,
and then the mixture so obtained may be heated to the temperatures mentioned above for the purposes of the post-crosslinking.

If the post-crosslinking is carried out after process step ii), first of all the untreated, water-absorbing polymer structures may be brought into contact with the salt in the manner described at the beginning, optionally in the absence of an organic solvent or in the form of fluid $F_1$, and then the water-absorbing polymer structures thus surface-modified are post-crosslinked at the surface.

In addition, a solution to the present problems is also provided by a water-absorbing polymer structure, comprising an inner region and an outer region surrounding the inner region, of which polymer structure more than about 80%, or at least about 85%, or at least about 90% by weight, or more than about 95% by weight, in each case relative to the water-absorbing polymer structure, are based on acrylic acid, of which from about 50 to about 90 mol %, or from about 60 to about 85 mol %, or from about 65 to about 80 mol %, may be neutralized, the water-absorbing polymer structure having the following properties:
  A1 a saline flow conductivity (SFC) determined in accordance with the test method described herein of more than about $115 \times 10^{-7}$ cm³s/g, or more than about $125 \times 10^{-7}$ cm³s/g, or more than about $135 \times 10^{-7}$ cm³s/g, or more than about $145 \times 10^{-7}$ cm³s/g, or more than about $165 \times 10^{-7}$ cm³s/g;
  B1 an absorption determined according to ERT 442.2-02 against a pressure of 0.7 psi ($AAP_{0.7}$) of more than about 25.9 g/g, or more than about 26.4 g/g, about more than 26.9 g/g, or more than about 27.5 g/g;
  C1 a retention (CRC) determined according to ERT 441.2-02 of at least about 25 g/g, at least about 27 g/g, more than about 28 g/g, or at least about 29 g/g; and
  D1 a particle size distribution with at least about 80% by weight, at least about 85% by weight, at least about 90% by weight, or at least about 95% by weight of the particles of the water-absorbing polymer structure in a particle size of from about 150 to about 850 µm, at least about 5% by weight, or at least about 8% by weight, or at least about 12% by weight, of the particles of water-absorbing polymer structure having a particle size in a range of from about 150 to about 250 µm. Furthermore, the amount of particles of water-absorbing polymer structure may be from about 150 to about 250 µm to lie from about 5 to about 30% by weight, or from about 7 to about 25% by weight, or from about 10 to about 20% by weight, or from about 11 to about 15% by weight, in each case based on the total amount of particles of water-absorbing polymer structure.

According to a particular embodiment of the water-absorbing polymer structures according to the invention, these may be characterized, in addition to the above mentioned properties A1 to D1, in particular in addition to the above-mentioned property A1, by the following property:
  E1 a PUP value determined according to EP 0 752 892 A1 of at least about 31 g/g, at least about 32 g/g, or at least about 33 g/g.

In this context, the water-absorbing polymer structures according to the invention may have, with a PUP value of at least about 31 g/g, or at least about 32 g/g, or at least about 33 g/g, a Saline Flow Conductivity (SFC), determined according to the herein-described test method, of more than about $100 \times 10^{-7}$ cm³ s/g.

A further solution to the present problems is provided by a water-absorbing polymer structure, comprising an inner region and an outer region surrounding the inner region, of which polymer structure at least about 80%, or at least about 90%, or at least about 95% by weight, in each case relative to the water-absorbing polymer structure, are based on acrylic acid, of from about 50 to about 90 mol %, or from about 60 to about 85 mol %, or from about 65 to about 80 mol %, are neutralized, the outer region of the water-absorbing polymer structure comprising a salt comprising a divalent or higher-valent cation of a metal, the water-absorbing polymer structure having the following properties:
  A2 a saline flow conductivity (SFC) determined in accordance with the test method described herein of more than about $89 \times 10^{-7}$ cm³s/g, or more than about $115 \times 10^{-7}$ cm³s/g, or more than about $125 \times 10^{-7}$ cm³s/g, more than about $135 \times 10^{-7}$ cm³s/g, or more than about $145 \times 10^{-7}$ cm³s/g, or more than about $160 \times 10^{-7}$ cm³s/g;
  B2 an absorption determined according to ERT 442.2-02 against a pressure of 0.7 psi ($AAP_{0.7}$) of more than about 24.7 g/g, or more than about 25.9 g/g, or more than about 26.5 g/g, or more than about 27 g/g, or more than about 27.5 g/g;
  C2 a retention (CRC) determined according to ERT 441.2-02 of at least about 25 g/g, or at least about 27 g/g, or more than about 27.2 g/g, more than about 28 g/g, at least about 29 g/g; and
  D2 a particle size distribution with at least about 80% by weight, or at least about 85% by weight, or at least about 90% by weight, or at least about 95% by weight of the particles of water-absorbing polymer structure in a particle size range of from about 150 to about 850 µm, at least about 5% by weight, or at least about 8% by weight, or at least about 12% by weight, of the particles of water-absorbing polymer structure having a particle size in a range of from about 150 to about 250 µm. Furthermore, for the amount of particles of water-absorbing polymer structure of from about 150 to about 250 µm of from about 5 to about 30% by weight, or from about 7 to about 25% by weight, or from about 10 to about 20% by weight, or from about 11 to about 15% by weight, in each case based on the total amount of particles of water-absorbing polymer structure.

According to another embodiment of the water-absorbing polymer structures according to the invention, these may be characterized, in addition to the above mentioned properties A2 to D2, in particular in addition to the above-mentioned property A1, by the following property:

E2 a PUP value determined according to EP 0 752 892 A1 of at least about 31 g/g, or at least about 32 g/g, or at least about 33 g/g.

In this context, the water-absorbing polymer structures according to the invention may have, with a PUP value of at least about 31 g/g, or at least about 32 g/g, or at least about 33 g/g, a Saline Flow Conductivity (SFC), determined according to the herein-described test method, of more than about $100 \times 10^{-7}$ cm$^3$s/g.

In connection with properties D1 and D2, in accordance with another embodiment of the present invention at least about 80% by weight, or at least about 85% by weight, at least 90% by weight, or at least about 95% by weight, of the particles of water-absorbing polymer structure have a particle size of from about 150 to about 850 μm, wherein, in each case based on the amount of particles having a particle size of from about 150 to about 850 μm, from about 1 to about 20% by weight, or from about 5 to about 17% by weight, or from about 7 to about 15% by weight, have a particle size in the range from about 150 to about 250 μm, from about 15 to about 79% by weight, or from about 20 to about 60% by weight, or from about 30 to about 50% by weight, have a particle size of from about 250 to about 600 μm, and the respective remaining amount of particles making up 100% by weight have a particle size in a range of from about 600 to about 850 μm.

In connection with properties D1 and D2, in another form of the present invention at least about 80% by weight, at least about 85% by weight, at least about 90% by weight, or at least about 95% by weight, of the particles of water-absorbing polymer structure have a particle size of from about 150 to about 850 μm, wherein, in each case based on the amount of particles having a particle size of from about 150 to about 850 μm, from about 1 to about 20% by weight, or from about 5 to about 17% by weight, or from about 7 to about 15% by weight, have a particle size of from about 150 to about 250 μm, from about 30 to about 79% by weight, or from about 40 to about 79% by weight, or from about 60 to about 78% by weight, have a particle size of from about 250 to about 600 μm, and the respective remaining amount of particles making up 100% by weight have a particle size in a range of from about 600 to about 850 μm.

As is generally customary in the case of water-absorbing polymers and described inter alia in DE 10 2004 005 417 A1 in paragraph [0055], the water-absorbing polymer structures according to the invention may have particles with sizes lying across the whole of a particle size range. In some cases, relatively small amounts also lie outside of from about 150 to about 850 μm. For example, particle size of from about 10 to about 1200 μm, or from about 40 to about 1000 μm, or from about 45 to about 850 μm as well as from about 100 to about 800 μm, or from about 100 to about 700 μm have been observed. For those particles size ranges too, in the case of a polymer structure according to the invention the comments made above in connection with D1 and D2 apply accordingly.

A solution to the problems mentioned at the beginning is also provided by a water-absorbing polymer structure that is obtainable by the process described above, the water-absorbing polymer structure comprising an inner region and an outer region surrounding the inner region, and the salt comprising the divalent or higher-valent cation of a metal and the at least one organic base as anion being present in the outer region of the water-absorbing polymer structure.

A further solution to the problems mentioned at the beginning is provided by a water-absorbing polymer structure, comprising an inner region and an outer region surrounding the inner region, a salt comprising a divalent or higher-valent cation of a metal and at least one organic base as anion being present in the outer region of the water-absorbing polymer structure, and the water-absorbing polymer structure having A3 a Saline Flow Conductivity (SFC) determined in accordance with the test method described herein of at least about $30 \times 10^{-7}$ cm$^3$s/g, or at least about $50 \times 10^{-7}$ cm$^3$s/g, or at least about $70 \times 10^{-7}$ cm$^3$s/g, or at least about $90 \times 10^{-7}$ cm$^3$s/g, or a SFC value of at least about $130 \times 10^{-7}$ cm$^3$s/g, or at least about $155 \times 10^{-7}$ cm$^3$s/g; and B3 an absorption determined according to ERT 442.2-02 against a pressure (AAP) of 0.7 psi of at least about 20 g/g, or at least about 22 g/g, or at least about 24 g/g, or at least about 26 g/g, or at least about 27 g/g.

According to another embodiment of these water-absorbing polymer structures according to the invention, these also have, in addition to the two above-mentioned properties (SFT value and AAP value), a PUP value determined according to EP 0 752 892 A1 of at least about 31 g/g, or at least about 32 g/g, or at least about 33 g/g. The water-absorbing polymer structures according to the invention, may have a PUP value of at least about 31 g/g, or of at least about 32 g/g, or of at least about 33 g/g, also have a Saline Flow Conductivity (SFC) determined according to the herein-described test method of more than about $100 \times 10^{-7}$ cm$^3$ s/g.

It is also possible to set upper limits for the properties such as SFC, AAP, CRC and PUP. For the SFC, such upper limits lie in some cases at about $180 \times 10^{-7}$ cm$^3$s/g or only at about $200 \times 10^{-7}$ cm$^3$s/g or sometimes also at about $250 \times 10^{-7}$ cm$^3$s/g or at about $350 \times 10^{-7}$ cm$^3$s/g or at about $500 \times 10^{-7}$ cm$^3$s/g. Upper limits for the AAP lie at about 30 g/g, in some cases at about 35 g/g, or at about 45 g/g. Upper limits for the CRC lie at about 35 g/g, in some cases at 45 g/g, or at about 50 g/g. For the PUP values, the upper limits generally lie at about 40 g/g, or at about 50 g/g, or at about 60 g/g.

As salt(s) comprising a divalent or higher-valent cation of a metal as well as at least one organic base as anion, such as given to those salts, cations, and anions that have already been mentioned at the beginning in connection with the process according to the invention.

At least about 50% by weight, or at least about 70% by weight, or at least about 90% by weight, of the water-absorbing polymer structure to be based on carboxylic-acid-group-carrying monomers, those carboxylic-acid-group-carrying monomers consisting of at least about 50% by weight, or at least about 70% by weight, acrylic acid, of which at least about 20 mol %, or at least 50 mol %, or from about 60 to 85 mol %, are neutralized.

Furthermore, the water-absorbing polymer structures according to the invention may be characterized in that the outer region of the water-absorbing polymer structures having a higher degree of crosslinking than the inner region of the water-absorbing polymer structures.

Water-absorbing polymer structures according to the invention include fibers, foams, or particles.

Polymer fibers according to the invention may be dimensioned so that they can be incorporated into or as yarns for textiles, and also directly into textiles. The polymer fibers may have a length of from about 1 to about 500 mm, or from about 2 to about 500 mm, or from about 5 to about 100 mm, and a diameter of from about 1 to about 200 Denier, or from about 3 to about 100 Denier, or from about 5 to about 60 Denier.

Polymer particles of the invention may be so dimensioned that they may have an average particle size in accordance with ERT 420.2-02 of from about 10 to about 3000 µm, or from about 20 to about 2000 µm, or from about 150 to about 850 µm or from about 150 to about 600 µm. The proportion of polymer particles may have a particle size of from about 300 to about 600 µm to be at least about 30% by weight, or at least about 40% by weight, or at least about 50% by weight, based on the total weight of the post-crosslinked, water-absorbing polymer particles.

A further solution to the problems mentioned at the beginning is provided by a composite comprising the above-defined water-absorbing polymer structures or the water-absorbing polymer structures obtainable by the process of the invention and a substrate. The water-absorbing polymer structures according to the invention and the substrate may be firmly joined to one another. As substrates there may be films of polymers, such as, for example, polyethylene, polypropylene or polyamide, metals, non-wovens, fluff, tissues, woven fabrics, natural, or synthetic fibers, or other foams. The composite according to the invention, in addition to comprising the water-absorbing polymer structures according to the invention and the substrate, may also comprise auxiliaries, such as, for example, thermoplastic materials.

In accordance with another embodiment of the composite according to the invention, the composite may be an absorbent layer, a core, or a wipe.

Absorbent layers according to the invention include those absorbent layers described as "absorbent members" in U.S. Pat. No. 5,599,335, U.S. Pat. No. 5,599,335 being incorporated herewith as reference only to the extent of "absorbent members" and the disclosure content of U.S. Pat. No. 5,599,335, especially in respect of fibers and auxiliaries contained in the absorbent layers and in respect of the processes for the preparation of the absorbent layers.

In accordance with another embodiment of the composite according to the invention, such as of the absorbent layer according to the invention, that composite or that absorbent layer comprises at least one region that contains the water-absorbing polymer structure according to the invention in an amount of about from about 15 to about 100% by weight, or from about 30 to about 100% by weight, or from about 50 to about 99.99% by weight, or from about 60 to 99.99% by weight, or from about 70 to about 99% by weight, in each case based on the total weight of the region of the composite or absorbent layer in question, that region having a size of at least about 0.01 cm$^3$, or at least about 0.1 cm$^3$, or at least about 0.5 cm$^3$.

Furthermore, the absorbent layer according to the invention may be characterized by a weight per unit area of at least about 0.02 g/cm$^2$, or at least about 0.03 g/cm$^2$, or from about 0.02 to about 0.12 g/cm$^2$, or from about 0.03 to about 0.11 g/cm$^2$, the absorbent layer moreover having a thickness of a maximum of about 20 mm, or a maximum of about 15 mm, or a maximum of 10 mm.

In accordance with another embodiment of the absorbent layer according to the invention, the absorbent layer has a surface area of a maximum of about 500 cm$^2$, or a maximum of about 350 cm$^2$, or a maximum of about 300 cm$^2$.

The preparation of the composite according to the invention may be effected by bringing the water-absorbing polymer structures according to the invention or the water-absorbing polymer structures obtainable by the process of the invention and the substrate and optionally the auxiliary into contact with one another. The contact may be made by wet-laid and air-laid methods, compacting, extruding and mixing.

In accordance with a form of the process according to the invention for the preparation of a composite, the process comprises the following process steps:

A) providing a substrate;
B) providing a water-absorbing polymer structure that is untreated but is already post-crosslinked at the surface;
C) providing a finely particulate component;
D) bringing the substrate into contact with the water-absorbing polymer structure;
E) bringing the water-absorbing polymer structure into contact with the finely particulate component; and
F) immobilizing at least a portion of the fine particles on the surface of the water-absorbing polymer structures.

Finely particulate component may be the finely particulate component already described as finely particulate component above in connection with the embodiment of the process according to the invention for the preparation of a water-absorbing polymer structure in which a powdered salt is used. An example is a mixture of powdered salt and powdered binder.

In accordance with a variant of this form of the process according to the invention for the preparation of a composite, the substrate and the water-absorbing polymer structure, which is untreated but is already post-crosslinked at the surface, may be first brought into contact with one another, such as by first providing the substrate and then applying, for example scattering, the polymer structure either uniformly or over specific areas of the substrate surface. The water-absorbing polymer structures located on the surface of the substrate may then brought into contact with the finely particulate component, for example by scattering the finely particulate component over the polymer structures located on the surfaces of the substrate. Finally, the immobilization of the finely particulate component on the surface of the polymer structures is effected, that immobilization being effected by the heating described above in connection with the process according to the invention for treatment of the surface of water-absorbing polymer structures. In that variant of the special form of the process according to the invention for the preparation of a composite, process step E) is therefore carried out after process step D).

In accordance with another embodiment of that form of the process according to the invention for the preparation of a composite, first of all the substrate is provided. Then the water-absorbing polymer structure, which is untreated but is already post-crosslinked at the surface, is brought into contact with the substrate, by first providing the substrate and then applying, scattering, the polymer structure either uniformly or over specific areas of the substrate surface. Before the polymer structure is brought into contact with the substrate surface, the water-absorbing polymer structures may be brought into contact with the finely particulate component, for example by mixing the finely particulate component with the polymer structure before it is scattered over the surface of the substrate. After the polymer structures have been brought into contact with the substrate, the immobilization of the finely particulate component on the surface of the polymer structures is effected. In that variant of the special form of the process according to the invention for the preparation of a composite, process step E) is therefore carried out before process step D).

The present invention relates also to the composite obtainable by the process described above.

The present invention relates also to chemical products comprising the polymer structures according to the invention or the composite. Chemical products may be foams, molded articles, fibers, foils, films, cables, sealing materials, fluid-absorbing hygiene articles, and carriers for plant- or fungus-growth-regulating compositions or plant protection active ingredients, additives for building materials, packaging materials or soil additives.

In addition, the present invention relates to the use of the water-absorbing polymer structures according to the invention, to the use of the water-absorbing polymer structures obtainable by the process of the invention, to the use of the composite or of the composite obtainable by the process described above in the above-mentioned chemical products, especially in hygiene products, for flood control, for insulation against water, for regulating the water content of soils or for treating foodstuffs.

The invention is described in greater detail below with reference to about test methods and non-limiting examples.

Test Methods

Determination of the SFC Value

The determination of the permeability in the swollen state (Saline Flow Conductivity=SFC) is effected in accordance with a method described in WO-A-95/22356. In a cylinder having a screen base, about 0.9 g of superabsorber material (in the case of particles, the entire particle fraction) is weighed in and carefully distributed over the surface of the screen. The superabsorber material is swelled in JAYCO synthetic urine for 1 hour against a pressure of 0.7 psi. After the swollen height of the superabsorber has been ascertained, 0.118M NaCl solution from a graded supply vessel is passed through the swollen gel layer at constant hydrostatic pressure. During the measurement, the swollen gel layer is covered with a special cylindrical screen which ensures a uniform distribution of the 0.118M NaCl solution above the gel and constant conditions (measurement temperature 20-25° C.) during the measurement in respect of the gel bed properties. The pressure acting on the swollen superabsorber is also 0.7 psi. With the aid of a computer and scales, the amount of fluid that passes through the gel layer as a function of time is determined at 20 second intervals within a time period of 10 minutes. The flow rate in g/s through the swollen gel layer is determined by means of regression analysis with extrapolation of the gradient, and determination of the midpoint, to the time point t=0 of the amount of flow within minutes 2 to 10. The SFC value (K) was given in cm³·s·g⁻¹ and calculated as follows:

$$K = \frac{F_s(t=0) \cdot L_0}{r \cdot A \cdot \Delta P_1} = \frac{F_s(t=0) \cdot L_0}{139506}$$

wherein
- $F_s(t=0)$ is the flow rate in g/s,
- $L_0$ is the thickness of the gel layer in cm,
- r is the density of the NaCl solution (1.003 g/cm³),
- A is the area of the upper side of the gel layer in the measuring cylinder (28.27 cm²),
- $\Delta P$ is the hydrostatic pressure load on the gel layer (4,920 dyne/cm²), and
- K is the SFC value.

Determination of the Retention

The retention, referred to as CRC, is determined in accordance with ERT 441.2-02, "ERT" representing "EDANA recommended Test" and "EDANA" representing European Disposables and Nonwovens Association.

Determination of Absorption Under Pressure

The absorption, referred to as AAP, against a pressure 0.7 psi is determined according to ERT 442.2-02.

Determination of Particle Size

The particle sizes are determined in the present case in accordance with ERT 420.2-02, the screens indicated herein being used.

EXAMPLES

A Preparation of SAP Particles

A monomer solution consisting of 640 g of acrylic acid, of which 75 mol % have been neutralized with sodium hydroxide solution (532.82 g of 50% NaOH), 801.32 g of water, 1.016 g of polyethylene glycol 300 diacrylate, 2.073 g of monoallyl polyethylene glycol 450 monoacrylic acid ester, is freed of dissolved oxygen by flushing with nitrogen and cooled to the starting temperature of 4° C. After the starting temperature has been reached, the initiator solution (0.6 g of sodium peroxydisulphate in 10 g of $H_2O$, 0.014 g of 35% hydrogen peroxide solution in 10 g of $H_2O$ and 0.03 g of ascorbic acid in 2 g of $H_2O$) was added. Once the final temperature of about 100° C. had been reached, the resulting gel was comminuted using a mincer and dried at 150° C. for 2 hours in a drying cabinet. The dried polymerizate was coarsely pounded, ground using a cutting mill SM 100 having 2 mm Conidur holes and screened to a powder having a particle size of from 150 to 850 μm, thus yielding powder A (particle sizes: on 150 μm mesh size 13%, on 300 μm mesh size 15%, on 400 μm mesh size 13%, on 500 μm mesh size 15%, on 600 μm mesh size 20%, on 710 to 850 μm mesh size 24%). The properties of the powder are given in Table 1.

Comparison Example 1

Conventional Surface Modification with Post-Crosslinker and Aluminum Sulphate 100 g of powder A are mixed with a solution consisting of 1.0 g of ethylene carbonate (EC), 0.6 g of $Al_2(SO_4)_3 \times 14H_2O$ and 3 g of deionized water, the solution being applied to the polymerizate powder located in a mixer by means of a syringe using a 0.45 mm cannula. Then powder A, coated with the aqueous solution, was heated in a circulating-air cabinet at 185° C. for 30 minutes. A powder A1 was obtained (particle sizes: on 150 μm mesh size 13%, on 300 μm mesh size 15%, on 400 μm mesh size 12%, on 500 μm mesh size 15%, on 600 μm mesh size 20%, on 710 to 850 μm mesh size 25%). The properties of the powder are given in Table 1.

Example 1

Surface Modification According to the Invention with a Solution of Post-Crosslinker and Aluminum Lactate 100 g of powder A are mixed with a solution consisting of 1.0 g of ethylene carbonate, 0.6 g of aluminum lactate and 3 g of deionized water, the solution being applied to the polymerizate powder located in a mixer by means of a syringe using a 0.45 mm cannula. Then powder A, coated with the aqueous solution, was heated in a circulating-air cabinet at 185° C. for 30 minutes. A powder A2 was obtained (particle sizes: on 150 μm mesh size 12%, on 300 μm mesh size 16%, on 400 μm mesh size 14%, on 500 μm mesh size 14%, on 600 μm mesh size 21%, on 710 to 850 μm mesh size 23%). The properties of the powder are given in Table 1.

Example 2

Surface Modification According to the Invention with Post-Crosslinker and Aluminum Lactate, Solid Before Post-Crosslinking 100 g of powder A are intimately mixed with 0.6 g of aluminum lactate powder (particle size: 85% in the range of from 45 to 150 μm, greater than 150 μm 9%, less than 45 μm 6%) for 10 minutes and mixed with a solution consisting of 1.0 g of ethylene carbonate and 3 g of deionized water, the solution being applied to the polymerizate powder located in a mixer by means of a syringe using a 0.45 mm cannula. Then powder A, coated with the aqueous solution, was heated in a circulating-air cabinet at 185° C. for 30 minutes. A powder A3 was obtained (particle sizes: on 150 μm mesh size 14%, on 300 μm mesh size 14%, on 400 μm mesh size 13%, on 500 μm mesh size 15%, on 600 μm mesh size 19%, on 710 to 850 μm mesh size 25%).

Example 3

Surface Modification According to the Invention with Post-Crosslinker and Aluminum Lactate, Solid after Post-Crosslinking 100 g of powder A are mixed with a solution consisting of 1.0 g of ethylene carbonate and 3 g of deionized water, the solution being applied to the polymerizate powder located in a mixer by means of a syringe using a 0.45 mm cannula. Then powder A, coated with the aqueous solution, was heated in a circulating-air cabinet at 185° C. for 30 minutes. That product was then intimately mixed with 0.6 g of aluminum lactate powder (particle size: 85% in the range of from 45 to 150 μm, greater than 150 μm 9%, less than 45 μm 6%) for 10 minutes. A powder A4 was obtained (particle sizes: on 150 μm mesh size 15%, on 300 μm mesh size 14%, on 400 μm mesh size 13%, on 500 μm mesh size 14%, on 600 μm mesh size 19%, on 710 to 850 μm mesh size 25%).

Example 4

Surface Modification According to the Invention with Post-Crosslinker and Aluminum Lactate, Liquid after Post-Crosslinking 100 g of powder A are mixed with a solution consisting of 1.0 g of ethylene carbonate and 3 g of deionized water, the solution being applied to the polymerizate powder located in a mixer by means of a syringe using a 0.45 mm cannula. Then powder A, coated with the aqueous solution, was heated in a circulating-air cabinet at 170° C. for 30 minutes. That product was then cautiously intimately mixed with a solution of 0.6 g of aluminum lactate in 3 g of deionized water for 30 minutes to form a powder. That mixing product was dried at 130° C. for 30 minutes, thus yielding powder A5 (particle sizes: on 150 μm mesh size 12%, on 300 μm mesh size 15%, on 400 μm mesh size 14%, on 500 μm mesh size 15%, on 600 μm mesh size 18%, on 710 to 850 μm mesh size 26%).

Example 5

Surface Modification According to the Invention with a Solution of Post-Crosslinker, Aluminum Lactate and Aluminum Sulphate 100 g of powder A are mixed with a solution consisting of 1.0 g of ethylene carbonate, 0.2 g of aluminum lactate, 0.4 g of aluminum sulphate and 3 g of deionized water, the solution being applied to the polymerizate powder located in a mixer by means of a syringe using a 0.45 mm cannula. Then powder A, coated with the aqueous solution, was heated in a circulating-air cabinet at 185° C. for 30 minutes. A powder A6 was obtained (particle sizes: on 150 μm mesh size 12%, on 300 μm mesh size 15%, on 400 μm mesh size 14%, on 500 μm mesh size 15%, on 600 μm mesh size 20%, on 710 to 850 μm mesh size 24%). The properties of the powder are given in Table 1.

Example 6

Surface Modification According to the Invention with a Solution of Post-Crosslinker, Aluminum Lactate and Aluminum Sulphate 100 g of powder A are mixed with a solution consisting of 1.0 g of ethylene carbonate, 0.3 g of aluminum lactate, 0.3 g of aluminum sulphate and 3 g of deionized water, the solution being applied to the polymerizate powder located in a mixer by means of a syringe using a 0.45 mm cannula. Then powder A, coated with the aqueous solution, was heated in a circulating-air cabinet at 190° C. for 30 minutes. A powder A7 was obtained (particle sizes: on 150 μm mesh size 12%, on 300 μm mesh size 15%, on 400 μm mesh size 13%, on 500 μm mesh size 15%, on 600 μm mesh size 20%, on 710 to 850 μm mesh size 25%). The properties of the powder are given in Table 1.

TABLE 1

| | Coating with | | | Properties | | |
|---|---|---|---|---|---|---|
| Powder | EC [% by wt] | Alsulphate [% by wt.] | Al lactate [% by wt.] | CRC [g/g] | AAP (0.7 psi) [g/g] | SFC** |
| A | 0 | 0 | 0 | 33.8 | 20* | |
| A1 | 1.0 | 0.6 | 0 | 29.6 | 23.7 | 54 |
| A2 | 1.0 | 0 | 0.6 | 29.7 | 25.3 | 74 |
| A6 | 1.0 | 0.4 | 0.2 | 28.9 | 24.0 | 101 |
| A7 | 1.0 | 0.3 | 0.3 | 28.2 | 24.6 | 110 |

*determined at 0.3 psi
**[×10$^{-7}$ cm$^3$s/g]

B. Preparation of SAP Particles

A monomer solution consisting of 260 g of acrylic acid, of which 70 mol % have been neutralized with sodium hydroxide solution (202.054 g of 50% NaOH), 505.899 g of water, 0.409 g of polyethylene glycol 300 diacrylate, 1.253 g of monoallyl polyethylene glycol 450 monoacrylic acid ester, is freed of dissolved oxygen by flushing with nitrogen and cooled to the starting temperature of 4° C. After the starting temperature has been reached, the initiator solution (0.3 g of sodium peroxydisulphate in 10 g of H$_2$O, 0.07 g of 35% hydrogen peroxide solution in 10 g of H$_2$O and 0.015 g of ascorbic acid in 2 g of H$_2$O) was added. Once the final temperature of about 100° C. had been reached, the resulting gel was comminuted in a mincer and dried at 150° C. for 2 hours in a drying cabinet. The dried polymerizate was coarsely pounded, ground using a cutting mill SM 100 having 2 mm Conidur holes and screened to give two powders B and C having a particle size of from 150 to 850 μm, which have the particle sizes given in Table 2.

TABLE 2

| Powder | 150 to 250 μm [%] | >250 to 600 μm [%] | >600 to 850 μm [%] |
|---|---|---|---|
| B | 8 | 42 | 50 |
| C | 12.5 | 75 | 12.5 |

Comparison Example 2

Conventional Surface Modification with Post-Crosslinker and Aluminum Sulphate 100 g of powder B are mixed with a solution consisting of 1.0 g of ethylene carbonate (EC), 0.6 g of $Al_2(SO_4)_3$ x14$H_2O$ and 3 g of deionized water, the solution being applied to the polymerizate powder located in a mixer by means of a syringe using a 0.45 mm cannula. Then powder B, coated with the aqueous solution, was heated in a circulating-air cabinet at 170° C. for 90 minutes. A powder B1 was obtained (particle sizes: on 150 μm mesh size 7%, on 250 μm mesh size 43%, on 600 to 850 μm mesh size 50%). The properties of the powder are given in Table 3.

Comparison Example 3

Conventional Surface Modification with Post-Crosslinker and Aluminum Sulphate

Comparison Example 2 was repeated with the difference that powder C was used instead of powder B. Powder C1 was thus obtained (particle sizes: on 150 μm mesh size 12%, on 250 μm mesh size 75.5%, on 600 to 850 μm mesh size 12.5%). The properties of the powder are given in Table 4.

Example 7

Surface Modification According to the Invention with a Solution of Post-Crosslinker and Solid Aluminum Lactate 100 g of powder B are mixed with a solution consisting of 1.0 g of ethylene carbonate, 0.6 g of solid aluminum lactate and 3 g of deionized water, the solution being applied to the polymerizate powder located in a mixer by means of a syringe using a 0.45 mm cannula. Then powder B, coated with the aqueous solution, was heated in a circulating-air cabinet at 185° C. for 30 minutes. A powder B2 was obtained (particle sizes: on 150 μm mesh size 9%, on 250 μm mesh size 40%, on 600 to 850 μm mesh size 51%). The properties of the powder are given in Table 3.

Example 8

Surface Modification According to the Invention with a Solution of Post-Crosslinker and Solid Aluminum Lactate Example 7 was repeated with the difference that powder C was used instead of powder B. Powder C2 was thus obtained (particle sizes: on 150 μm mesh size 11.5%, on 300 μm mesh size 76%, on 600 to 850 μm mesh size 12.5%). The properties of the powder are given in Table 4.

Example 9

Surface Modification According to the Invention with a Solution of Post-Crosslinker and Aluminum Lactate Solution 100 g of powder B are mixed with a first solution consisting of 1.0 g of ethylene carbonate and 1.457 g of deionized water and 0.6 g of aluminum lactate in the form of a 28% NaOH-stabilized aluminum lactate solution as second solution, the solutions being applied to the polymerizate powder located in a mixer by means of a syringe using a 0.45 mm cannula. For the preparation of the NaOH-stabilized aluminum lactate solution, 0.0625 mol (7.38 g) of sodium aluminate are dissolved in 15 ml of water, followed by 0.0475 mol of NaOH (2.5 ml of a 50% aqueous NaOH solution), to which solution there is then slowly added a mixture of 85% lactic acid, diluted in 20 ml of water, until a pH value of 4.5 is obtained (0.29 mol of lactic acid=31.0 g). Then powder B, coated with the aqueous solutions, was heated in a circulating-air cabinet at 185° C. for 30 minutes. A powder B3 was obtained (particle sizes: to 150 μm mesh size 9%, to 250 μm mesh size 40%, to 600 to 850 μm mesh size 51%). The properties of the powder are given in Table 3.

Example 10

Surface Modification According to the Invention with a Solution of Post-Crosslinker and Aluminum Lactate Solution Example 9 was repeated with the difference that powder C was used instead of powder B. Powder C3 was thus obtained (particle sizes: on 150 μm mesh size 11.5%, on 250 μm mesh size 76%, on 600 to 850 μm mesh size 12.5%). The properties of the powder are given in Table 4.

Example 11

100 g of powder B are intimately mixed with 0.6 g of aluminum lactate powder (particle size: 85% in the range of from 45 to 150 μm, greater than 150 μm 9%, less than 45 μm 6%) for 10 minutes and mixed with a solution consisting of 1.0 g of ethylene carbonate and 3 g of deionized water, the solution being applied to the polymerizate powder located in a mixer by means of a syringe using a 0.45 mm cannula. Then powder B, coated with the aqueous solution, was heated in a circulating-air cabinet at 170° C. for 90 minutes. A powder B4 was obtained (particle sizes: on 150 μm mesh size 14%, on 300 μm mesh size 13%, on 400 μm mesh size 13%, on 500 μm mesh size 15%, on 600 μm mesh size 19%, on 710 to 850 μm mesh size 25%).

Example 12

Example 8 was repeated with the difference that powder C was used instead of powder B. Powder C4 was thus obtained (particle sizes: on 150 μm mesh size 11.5%, on 300 μm mesh size 76%, on 600 μm mesh size 12.5%).

TABLE 3

| Powder | Coating with | | | Properties | | |
| --- | --- | --- | --- | --- | --- | --- |
| | EC [% by wt] | Al sulphate [% by wt.] | Al lactate [% by wt.] | CRC [g/g] | AAP (0.7 psi) [g/g] | SFC* |
| B  | 0   | 0   | 0             | 30.5 | 26.2 | 57  |
| B1 | 1.0 | 0.6 | 0             | 29.5 | 25.0 | 90  |
| B2 | 1.0 | 0   | 0.6 (solid)   | 29.5 | 26.8 | 159 |
| B3 | 1.0 | 0   | 0.6 (solution)| 29.1 | 27.8 | 160 |

*[×10$^{-7}$ cm$^3$/g]

TABLE 4

| Powder | Coating with | | | Properties | | |
| --- | --- | --- | --- | --- | --- | --- |
| | EC [% by wt] | Al sulfate [% by wt.] | Al lactate [% by wt.] | CRC [g/g] | AAP (0.7 psi) [g/g] | SFC* |
| C  | 0   | 0   | 0             | 30.8 | 27.5 | 48  |
| C1 | 1.0 | 0.6 | 0             | 29.1 | 24.9 | 115 |
| C2 | 1.0 | 0   | 0.6 (solid)   | 28.8 | 27.6 | 134 |
| C3 | 1.0 | 0   | 0.6 (solution)| 29.1 | 24.9 | 160 |

*[×10$^{-7}$ cm$^3$/g]

C. Preparation of SAP Particles

The preparation of SAP particles according to Example B was repeated, whereby two powders D and E were obtained, which have the particle sizes given in Table 5:

TABLE 5

| Powder | 150 to 300 μm [%] | >300 to 600 μm [%] | >600 to 850 μm [%] |
| --- | --- | --- | --- |
| D | 13   | 37 | 50   |
| E | 12.5 | 75 | 12.5 |

Example 13

100 g of powder E are treated as described in Example 7, whereby, however, differing from Example 7, heating was carried out at 170° C. for 90 minutes. A powder E1 was obtained. The properties of this powder are given in Table 6.

Example 14

100 g of powder E are treated as described in Example 9, whereby, however, differing from Example 9, heating was carried out at 170° C. for 90 minutes. A powder E2 was obtained. The properties of this powder are given in Table 6.

TABLE 6

| Powder | Coating with | | | Properties | | |
| --- | --- | --- | --- | --- | --- | --- |
| | EC [wt. %] | Al sulfate [wt. %] | Al lactate [wt. %] | CRC [g/g] | PUP [g/g] | SFC* |
| E  | 0   | 0 | 0              | 29.0 | 33.3 | 71  |
| E1 | 1.0 | 0 | 0.6 (solid)    | 28.9 | 32.8 | 104 |
| E2 | 1.0 | 0 | 0.6 (solution) | 29.1 | 32.4 | 148 |

*[×10$^{-7}$ cm$^3$/g]

Example 15

100 g of powder D are treated as described in Example 7, whereby, however, differing from Example 7, heating was carried out at 170° C. for 90 minutes. A powder D1 was obtained. The properties of this powder are given in Table 7.

Example 16

100 g of powder D are treated as described in Example 9, whereby, however, differing from Example 9, heating was carried out at 170° C. for 90 minutes. A powder D2 was obtained. The properties of this powder are given in Table 7.

TABLE 7

| Powder | Coating with | | | Properties | | |
| --- | --- | --- | --- | --- | --- | --- |
| | EC [wt. %] | Al sulfate [wt. %] | Al lactate [wt. %] | CRC [g/g] | PUP [g/g] | SFC* |
| D  | 0   | 0 | 0              | 29.4 | 33.1 | 68  |
| D1 | 1.0 | 0 | 0.6 (solid)    | 29.6 | 33.3 | 131 |
| D2 | 1.0 | 0 | 0.6 (solution) | 29.1 | 33.1 | 176 |

*[×10$^{-7}$ cm$^3$/g]

The invention claimed is:

1. A process for the preparation of a water-absorbing polymer structure, comprising the following process steps:
   i) providing an untreated, water-absorbing polymer structure; and
   ii) bringing the untreated, water-absorbing polymer structure into contact with from about 0.1 to about 5 wt % based on the weight of the untreated, water-absorbing polymer structure, of a salt comprising at least about 50 wt % of the salt, of aluminum lactate, and of which more than about 80% by weight, relative to the water-absorbing polymer structure, are based on acrylic acid, of which in a range of from about 50 to about 85 mol % are neutralized, the water-absorbing polymer structure having the following properties:

A1 a saline flow conductivity (SFC) determined in accordance with the test method described herein of from about 10×10$^7$ cm$^3$s/g to about 180×10$^7$ cm$^3$s/g;

B1 a retention (CRC) determined according to ERT 441.2-02 of at least about 25 g/g; and C1 a particle size distribution with at least about 80% by weight of the particles of the water-absorbing polymer structure in a particle size range of from about 150 to about 850 μm, at least about 5% by weight of the particles of water-absorbing polymer structure having a particle size in a range of from about 150 to about 250 μm.

2. The process according to claim 1, wherein the salt comprises from about 0.6 wt % to about 2 wt % based on the water-absorbing polymer structure, of aluminum lactate.

3. The process according to claim 1, wherein the salt comprises from about 0.6 wt % to about 1 wt % based on the water-absorbing polymer structure, of aluminum lactate.

4. The process according to claim 1, wherein the salt comprises at least about 75 wt % of the salt, of aluminum lactate.

5. The process according to claim 1, wherein the salt comprises at least about 100 wt % of the salt, of aluminum lactate.

6. The process according to claim 1, wherein the salt comprises from about 0.2 wt % to about 1 wt % based on the water-absorbing polymer structure of aluminum lactate and an amount of aluminum sulfate wherein the amount of aluminum lactate and aluminum sulfate is at least 0.6 wt % based on the water-absorbing polymer structure.

7. The process according to claim 1, wherein in process step ii) the untreated, water-absorbing polymer structure is brought into contact with the salt in the presence of at most about 15% by weight, based on the weight of the untreated, water-absorbing polymer structure, of a solvent.

8. A water-absorbing polymer structure comprising,
an untreated, water absorbing polymer structure comprising
   (α1) from about 20 to about 99.999% by weight, polymerized, ethylenically unsaturated, acid-group-carrying monomers or their salts or polymerized, ethylenically unsaturated monomers containing a protonated or quaternized nitrogen atom, or mixtures thereof; and
   (α2) from 0.001 to about 0.5% by weight of the part (α1), of a crosslinker;
wherein the untreated water-absorbing polymer structure forms an inner region and
an outer region surrounding the inner region, wherein the outer region comprises from about 0.1 to about 5 wt % based on the weight of the untreated, water-absorbing polymer structure, of a salt comprising at least about 50 wt % of the salt, of aluminum lactate, and
of which more than about 80% by weight, relative to the water-absorbing polymer structure, are based on acrylic acid, of which in a range of from about 50 to about 85 mol % are neutralized, the water-absorbing polymer structure having the following properties:
   A1 a saline flow conductivity (SFC) determined in accordance with the test method described herein of from about $10 \times 10^7$ cm$^3$s/g to about $180 \times 10^7$ cm$^3$s/g;
   B1 a retention (CRC) determined according to ERT 441.2-02 of at least about 25 g/g; and
   C1 a particle size distribution with at least about 80% by weight of the particles of the water-absorbing polymer structure in a particle size range of from about 150 to about 850 μm, at least about 5% by weight of the particles of water-absorbing polymer structure having a particle size in a range of from about 150 to about 250 μm.

9. The water-absorbing polymer structure according to claim 8, wherein the salt comprises at least about 75 wt % of the salt, of aluminum lactate.

10. The water-absorbing polymer structure according to claim 8, wherein the salt comprises at least about 100 wt % of the salt, of aluminum lactate.

11. The water-absorbing polymer structure according to claim 8, wherein the salt comprises from about 0.6 wt % to about 2 wt % based on the water-absorbing polymer structure, of aluminum lactate.

12. The water-absorbing polymer structure according to claim 8, wherein the salt comprises from about 0.6 wt % to about 1 wt % based on the water-absorbing polymer structure, of aluminum lactate.

13. The water-absorbing polymer structure according to claim 8, wherein the salt comprises from about 0.2 wt % to about 1 wt % based on the water-absorbing polymer structure of aluminum lactate and an amount of aluminum sulfate wherein the amount of aluminum lactate and aluminum sulfate is at least 0.6 wt % based on the water-absorbing polymer structure.

14. The water-absorbing polymer structure according to claim 8, wherein the outer region further comprises from about 0.01 wt % to about 1 wt % based on the water-absorbing polymer structure, of aluminum sulfate.

15. A composite comprising a water-absorbing polymer structure according to claim 8 and a substrate.

* * * * *